US00PP07791P

United States Patent [19]

Drewlow

[11] Patent Number: Plant 7,791

[45] Date of Patent: Feb. 18, 1992

[54] IMPATIENS PLANT NAMED ROSETTA

[75] Inventor: Lyndon W. Drewlow, Ashtabula, Ohio

[73] Assignee: Mikkelsens, Inc., Ashtabula, Ohio

[21] Appl. No.: 607,023

[22] Filed: Oct. 31, 1990

[51] Int. Cl.[5] ..... A01H 5/00

[52] U.S. Cl. ..... Plt./68

[58] Field of Search ..... Plt. 68

*Primary Examiner*—James R. Feyrer

*Attorney, Agent, or Firm*—Foley & Lardner

[57] ABSTRACT

A new and distinct cultivar of Impatiens plant named Rosetta, characterized by its rose pink flowers, large flower diameter, light green pedicels, dark green leaves with reddish purple cast, early flowering response, medium height, and mounded habit.

1 Drawing Sheet

The present invention comprises a new and distinctive cultivar of Impatiens plant, botanically known as *Impatiens*, and referred to by the cultivar name Rosetta. Rosetta was developed by me through controlled breeding by crossing Equinox, disclosed in U.S. Plant Pat. No. 6,297 (seed parent) with Mikkelsen Seedling No. 86-353-4 (pollen parent).

Asexual reproduction by terminal or stem cuttings has shown that the unique features of this new impatiens are stabilized and are produced true to type in successive propagations.

The following combination of characteristics distinguish Rosetta from both its parent varieties and other cultivated impatiens of this type known and used in the floriculture industry. Characteristics are with reference to comparison cultivars Equinox and Aurora (disclosed in U.S. Plant Pat. No. 6,298).

Color references are to The Royal Horticultural Society Colour Chart (R.H.S.).

1. Rosetta has rose pink flowers (68C to 68D) while Equinox has flesh pink flowers (36C) and Aurora has deeper rose pink flowers (55B).

2. Rosetta has a larger flower (6.0 to 6.5 cm in diameter) than both Equinox, which has a 5.5 to 6.0 cm flowers, and Aurora, which has a 4 to 5 cm flower diameter.

3. Rosetta has flower pedicels which are light green in color; Equinox has a medium red pedicel and Aurora has a deep red pedicel.

4. Rosetta has similar dark green leaves with a reddish purple cast as Aurora and Equinox, but Rosetta has no variegation. Equinox has a small area near the base of the leaf near the midrib with cream variegation, while Aurora has a large area of cream around the midrib.

5. Rosetta has a finely serrated leaf margin while Equinox and Aurora have entire leaf margins.

6. Rosetta has the least amount of red pigmentation in the stem, with Aurora having the most and Equinox intermediate between the two.

7. Rosetta is 4 to 7 days earlier in blooming than Equinox and Aurora.

8. Rosetta and Equinox usually have one flower bud per leaf axil while Aurora usually has two.

9. Rosetta has leaves that are intermediate in size (11–12 cm long and 2.25 to 2.5 cm wide) compared to Equinox (14–16 cm long and 3–4 cm wide) and Aurora (10–12 cm long and 2.5 to 3.5 cm wide).

10. Rosetta and Equinox are mounded, intermediate height cultivars, while Aurora is a much shorter growing mounded plant.

The accompanying colored photograph is a front perspective view of Rosetta showing the colors as true as reasonably possible to obtain in a colored reproduction of this type. The photo was taken in March 1990 under natural light on an overcast day under double poly greenhouse covering at Ashtabula, Ohio.

The following is a detailed description of Rosetta, based on plants produced in greenhouses in Ashtabula, Ohio during the summer season of the year. Plants are grown in 15 cm pots and measurements were taken 16 weeks after rooted cuttings were planted. Height measurements were taken from the soil line of the container. The plants were grown at 65°–68° F. night temperatures, under 3500 to 4500 foot candles of light, and 240 ppm nitrogen, 240 ppm potassium, and 175 ppm phosphorous nutritional levels with trace elements added. Habit of growth, foliage coloration, leaf variegation, size of leaves and flower size will be greatly influenced by nutritional and environmental conditions. Color references are made to The Royal Horticultural Society Colour Chart (R.H.S.) except where general terms of ordinary dictionary significance are used.

Parentage: A controlled cross between female parent Equinox and male parent Mikkelsen Seedling No. 86-3534.

Propagation:

A. *Type cutting.*—Stem 15 mm long will develop to 4 to 5 cm long in 18 to 21 days.

B. *Time to initiate roots.*—8–10 days at 23° C. summer; 10–12 days at 20° C. winter.

C. *Rooting habit.*—Heavy, fibrous.

Plant Description: Habit of growth, foliage coloration and size of leaf will be greatly influenced by nutritional and environmental conditions. Thus, data that follows was taken from plants grown under the conditions stated above.

A. *Form and habit of growth.*—Mounded; highly self-branched; intermediate in height; flowers over the top of leaf canopy; continuous flowering; vigorous growing flowering herb.

B. *Foliage description.*—Dark green with reddish purple cast with reddish purple midrib. Leaves have no variegation. 1. Size: 11 to 12 cm long and 2.25 to 2.5 cm wide for an average mature leaf. 2. Shape: Lanceolate with acuminate apex.

3. Texture: Both upper and lower surfaces are glabrous. 4. Margin: Finely serrated with fine ciliate. 5. Color: Young foliage top side, 147A; under side 183B. Mature foliage top side 147A; under side 183B. 6. Venation: Pinnate; red in color.

Flowering Description:

A. *Flowering habits.*—Flowers continuously from leaf whorl in a progressively orderly manner with one flower per leaf axil. When the last flower in a leaf whorl opens the first flower in the leaf whorl above starts to open. It takes 5 to 7 days for a mature bud to fully open, with the flowers lasting two weeks or longer depending on the environment.

B. *Natural flowering season.*—Indeterminant and continuous. Quantity of flowering increases with increasing levels of light.

C. *Flower buds.*—Ellipsoidal, flowers perfect; reddish spur (4.5 cm) on mature bud with the throat behind the ovary and orginating from the major sepal.

D. *Flowers borne.*—Individual light green pedicels from a whorl of 3 to 4 leaves, flowering progressively around the whorl as buds and leaves develop. Leaf axils have one flower each.

E. *Quantity of flowers.*—Very floriferous because of highly self-branched nature of plant and long lasting flowers; flowers open at two leaf whorls on a branch; flower development is continuous and above leaf canopy.

F. *Diameter of flower.*—6.0 to 6.5 cm.

G. *Petals.*—1. Shape: Heart-shaped; standard is largest petal. 2. Color: Top side when opening 68C to 68D with 57B eye, fading to 73D. Under side 68D. 3. Number of petals: Five. 4. Size of petals: Standard — 4.0 cm wide by 2.8 cm long; two equal lobes, shallow cut. Wings — 2.5 cm wide by 3.0 cm long; two unequal lobes, intermediate cut. Keel — 3.1 cm wide by 3.0 cm long; two unequal lobes, deep cut.

Reproductive Organs:

1. Stamens.—Five in number. Anther shape is hooded; cream in color with reddish tint. Pollen color is cream.
2. Pistils.—Stigma shape is five segmented column; cream with reddish tint. Style color is cream with reddish tint. Ovaries, five in number; 4 mm in size; color is green with slight reddish tint.

Disease Resistance: No significant disease and insect problems to date.

OTHER IMPORTANT CHARACTERISTICS

1. Self-branching, early flowering nature allows Rosetta to be grown in 10 cm pots, but it is also vigorous enough so that it can be grown in 15-25 cm containers.

2. Rosetta has the ability to bloom continuously in both high temperatures and sunlight, as well as cool temperatures (40°-50° F.). Thus, the growing season has been expanded.

I claim:

1. A new and distinct cultivar of Impatiens plant named Rosetta, as illustrated and described.

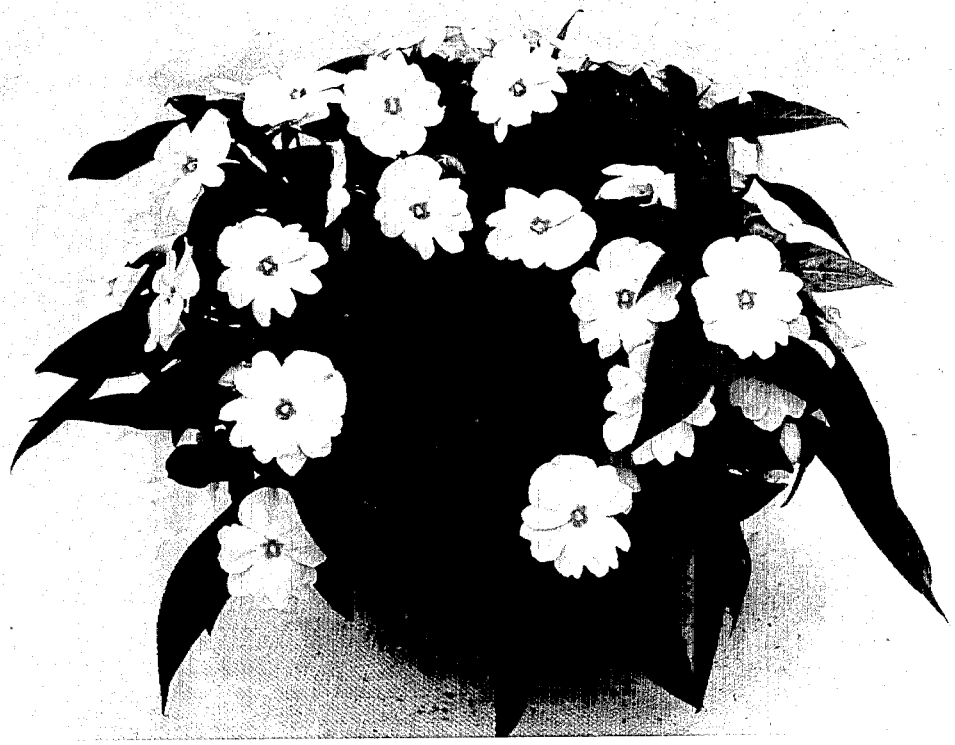

* * * * *